(12) United States Patent
Buettner-Janz et al.

(10) Patent No.: US 9,308,100 B2
(45) Date of Patent: Apr. 12, 2016

(54) INTERVERTEBRAL DISC PROSTHESIS WITH A MOTION-ADAPTED EDGE FOR THE LUMBAR AND CERVICAL SPINE

(76) Inventors: Karin Buettner-Janz, Berlin (DE); Eiko Buettner, Berlin (DE)

( * ) Notice: Subject to any disclaimer, the term of this patent is extended or adjusted under 35 U.S.C. 154(b) by 1138 days.

(21) Appl. No.: 11/379,086

(22) Filed: Apr. 18, 2006

(65) Prior Publication Data

US 2006/0235527 A1 Oct. 19, 2006

Related U.S. Application Data

(63) Continuation-in-part of application No. PCT/DE2005/001885, filed on Oct. 18, 2005.

(30) Foreign Application Priority Data

Oct. 18, 2004 (WO) ................ PCT/DE2004/002332

(51) Int. Cl.
*A61F 2/44* (2006.01)
*A61F 2/30* (2006.01)

(52) U.S. Cl.
CPC ..... *A61F 2/4425* (2013.01); *A61F 2002/30616* (2013.01); *A61F 2002/30663* (2013.01); *A61F 2002/30841* (2013.01); *A61F 2002/443* (2013.01); *A61F 2310/00023* (2013.01);
(Continued)

(58) Field of Classification Search
USPC ............... 623/17.11–17.16; 606/61, 246–279
See application file for complete search history.

(56) References Cited

U.S. PATENT DOCUMENTS

| | | | | |
|---|---|---|---|---|
| 4,997,432 A | * | 3/1991 | Keller | ........................ 623/17.11 |
| 5,258,031 A | | 11/1993 | Salib et al. | |
| 5,401,269 A | * | 3/1995 | Buttner-Janz et al. | ..... 623/17.15 |

(Continued)

FOREIGN PATENT DOCUMENTS

| | | |
|---|---|---|
| DE | 30 23 353 A1 | 4/1981 |
| DE | 3023353 A1 | 4/1981 |

(Continued)

OTHER PUBLICATIONS

Bomley, Anna, Spinal Devices: Market Opportunities and Technology Trends, Clinical Reports, CBS925, PJB Publications, Ltd., Jun. 2004, Surrey, UK.

(Continued)

*Primary Examiner* — Jan Christopher Merene
(74) *Attorney, Agent, or Firm* — Joyce von Natzmer; Agris & von Natzmer LLP

(57) ABSTRACT

The invention relates to an intervertebral disc prosthesis for the total replacement of the intervertebral disc within the lumbar and cervical spine. For a two part as well as for a three part intervertebral disc prosthesis, according to the invention, in accordance to the design of the edges of the sliding partners, there are aspects for at least one of the sliding partners, in which there is an wavelike design of the edge, as the respectively different high edge regions preferably fluently merge. A significant advantage of the two part intervertebral disc prostheses, according to the invention, compared to the present state of the art of already known prostheses, is that as a result of a transfer of load across a large surface area due to the spherical sliding surfaces, the maximal possible inclination of the sliding partners towards each other in a dorsoventral and laterolateral direction and/or the extent of axial rotation can, according to the invention, be defined through the wavelike design of the edge regions.

30 Claims, 10 Drawing Sheets

(52) U.S. Cl.
CPC .................. *A61F2310/00029* (2013.01); *A61F 2310/00131* (2013.01); *A61F 2310/00269* (2013.01)

(56) References Cited

U.S. PATENT DOCUMENTS

| | | | |
|---|---|---|---|
| 5,425,773 A * | 6/1995 | Boyd et al. | 623/17.15 |
| 5,556,431 A * | 9/1996 | Buttner-Janz | 623/17.15 |
| 6,145,421 A | 11/2000 | Gordon et al. | |
| 6,517,580 B1 | 2/2003 | Ramadan et al. | |
| 6,706,068 B2 | 3/2004 | Ferree | |
| 6,966,929 B2 * | 11/2005 | Mitchell | 623/17.11 |
| 7,083,649 B2 * | 8/2006 | Zucherman et al. | 623/17.11 |
| 7,166,130 B2 * | 1/2007 | Ferree | 623/17.15 |
| 7,182,784 B2 * | 2/2007 | Evans et al. | 623/17.15 |
| 7,566,346 B2 * | 7/2009 | Kirschman | 623/17.14 |
| 2001/0027343 A1 * | 10/2001 | Keller | 623/11.11 |
| 2001/0032017 A1 * | 10/2001 | Alfaro et al. | 623/17.11 |
| 2003/0135278 A1 | 7/2003 | Eckman | |
| 2003/0191534 A1 * | 10/2003 | Viart et al. | 623/17.15 |
| 2004/0117022 A1 * | 6/2004 | Marnay et al. | 623/17.16 |
| 2004/0133278 A1 | 7/2004 | Marino et al. | |
| 2004/0143332 A1 * | 7/2004 | Krueger et al. | 623/17.14 |
| 2004/0199253 A1 | 10/2004 | Link et al. | |
| 2005/0027364 A1 * | 2/2005 | Kim et al. | 623/17.13 |
| 2005/0251261 A1 * | 11/2005 | Peterman | 623/17.14 |
| 2006/0095132 A1 * | 5/2006 | Kirschman | 623/17.14 |
| 2006/0136062 A1 * | 6/2006 | DiNello et al. | 623/17.14 |
| 2006/0235528 A1 | 10/2006 | Buettner-Janz | |
| 2006/0235531 A1 | 10/2006 | Buettner-Janz | |
| 2006/0241772 A1 | 10/2006 | Buettner-Janz et al. | |
| 2007/0021837 A1 * | 1/2007 | Ashman | 623/17.16 |
| 2007/0173942 A1 * | 7/2007 | Heinz et al. | 623/17.15 |
| 2007/0299524 A1 * | 12/2007 | Rivin | 623/17.13 |
| 2008/0133013 A1 * | 6/2008 | Duggal et al. | 623/17.16 |

FOREIGN PATENT DOCUMENTS

| | | |
|---|---|---|
| DE | 35 29 761 C2 | 8/1985 |
| DE | 3529761 C2 | 6/1994 |
| DE | 102 42 329 A1 | 4/2004 |
| DE | 10242329 A1 | 4/2004 |
| DE | 2004002332 | 6/2005 |
| DE | 2005001885 | 12/2005 |
| EP | 0 560 141 B1 | 2/1993 |
| EP | 0560141 B1 | 10/1996 |
| WO | 2004/064692 A | 8/2004 |
| WO | WO 2004/064692 | 8/2004 |
| WO | PCT/DE2005/001885 | 1/2006 |

OTHER PUBLICATIONS

Bomley, Anna, Spinal Devices: Market opportunity and technology trends. Clinica Reports, Jun. 2004, PJB Publications, Ltd., Surrey, United Kingdom.

* cited by examiner

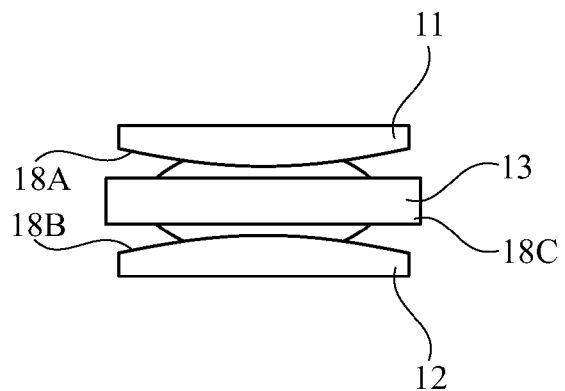
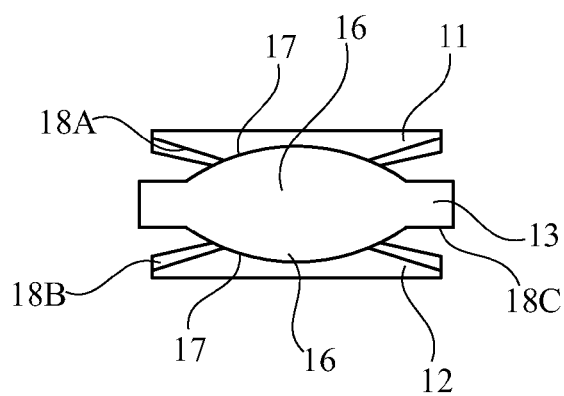
Fig. 2a   Fig. 2b
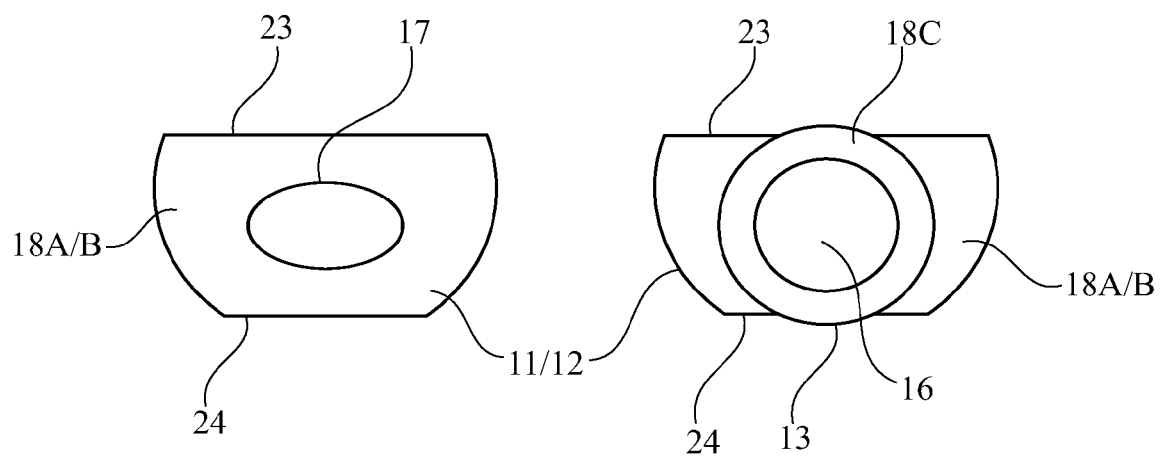
Fig. 3a   Fig. 3b

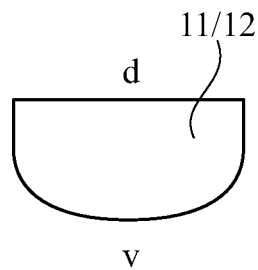
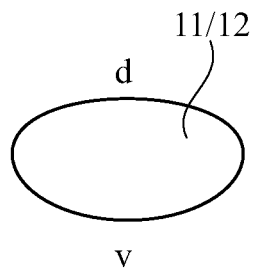
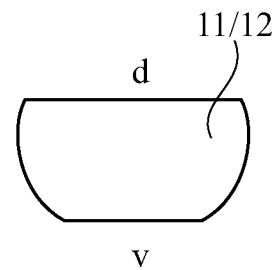
Fig. 4a  Fig. 4b  Fig. 4c
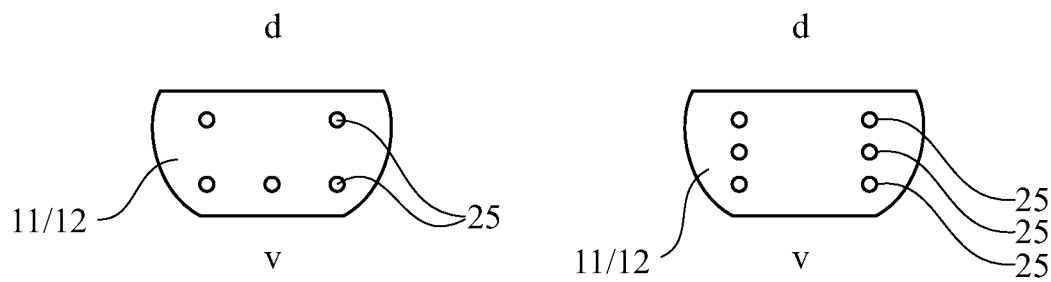
Fig. 5a  Fig. 5b

INTERVERTEBRAL DISC PROSTHESIS WITH A MOTION-ADAPTED EDGE FOR THE LUMBAR AND CERVICAL SPINE

CROSS REFERENCE SECTION

This is a continuation-in-part application of international application no. PCT/DE2005/001885, filed Oct. 18, 2005 designating the U.S. and claiming priority to international application no. PCT/DE2004/002332, filed Oct. 18, 2004. Both of these applications are incorporated herein by reference in their entirety.

FIELD OF THE INVENTION

The invention relates to an intervertebral disc prosthesis for the total replacement of an intervertebral disc of the lumbar and cervical spine.

BACKGROUND OF THE INVENTION

The idea of function-retaining artificial replacements for intervertebral discs is younger than that for replacements of artificial joints of extremities, but in the meantime about 50 years old [Büttner-Janz, Hochschuler, McAfee (Eds.): The Artificial Disc. Springer Verlag, Berlin, Heidelberg, New York 2003]. It results from biomechanical considerations, unsatisfactory results of fusion surgeries, disorders adjacent to fusion segments and from the development of new materials with greater longevity.

The publications and other materials, including patents, used herein to illustrate the invention and, in particular, to provide additional details respecting the practice are incorporated herein by reference.

By means of function-retaining disc implants it is possible to avoid fusion surgery, i.e. to maintain, or to restore the mobility within the intervertebral disc space. In an in-vitro experiment it is also possible to achieve a normalization of the biomechanical properties of the motion segment to a large extent through the implantation of an artificial intervertebral disc after a nucleotomy.

Implants for the replacement of the whole intervertebral disc differ from those for the replacement of the nucleus pulposus. Accordingly, implants for the total replacement of the intervertebral disc are voluminous; they are implanted via a ventral approach. An implantation of a prosthesis for total replacement of the intervertebral disc immediately after a standard nucleotomy can therefore not be carried out.

The indication for a function-retaining intervertebral disc replacement as an alternative to the surgical fusion includes, besides the painful discopathy, also pre-operated patients with a so-called post discectomy syndrome, patients with a recurrent herniated intervertebral disc within the same segment and patients having a pathology within the neighbouring intervertebral disc as a consequence fusion surgery.

Presently, a total of more than 10 different prostheses are clinically used for the total replacement of intervertebral discs. For the lumbar spine the CHARITÉ Artificial Disc, the PRODISC, the MAVERICK, the FLEXICORE and the MOBIDISC (Overview in Clinical Reports, PJB Publications Ltd., June 2004) are particularly well known, and for the cervical spine the BRYAN prosthesis, the PRESTIGE LP prosthesis, the PRODISC-C and the PCM prosthesis, which will be described below.

The PRODISC prosthesis for the lumbar spine is being implanted since 1999, following its further development to the PRODISC II. Although with respect to its components a three-part intervertebral disc prosthesis, it is functionally a two-part prosthesis with its sliding partners made of metal and polyethylene. Implantations of the PRODISC are carried out in the lumbar spine and with an adapted model of the prosthesis, the PRODISC-C, also in the cervical spine. Different sizes, heights (achieved by the polyethylene core) and angles of lordosis (achieved by the metal endplates) are available. Bending forward and backward as well as to the right and left is possible to the same extent of motion; the axial rotation is not limited in the construction.

The same applies to both two-part prostheses for the cervical spine, the PCM prosthesis with its sliding partners metal and polyethylene and the PRESTIGE LP prosthesis with its sliding partners metal-metal. As special feature of the construction of the PRESTIGE LP prosthesis it has the possibility for an anterior-posterior translation, due to the horizontal ventrally prolonged concavity, which, in a frontal section, has the same radius as the convexity.

The Maverick MAVERICK and the FLEXICORE for the lumbar spine are functionally two-part prostheses with spherical convex-concave sliding partners, both with sliding partners made of metal. In contrast, the MOBIDISC is functionally a three-part prosthesis with sliding partners of metal-polyethylene and two articulation surfaces. One area is a segment of a sphere, as it is in the three afore mentioned prostheses, with a convex and a concave surface of the articulating partners each of the same radius, the other area of the MOBIDISC being plane. Although a limitation of the axial rotation is planned within the plane section, it is not limited within the convex-concave area of articulation. In contrast the FLEXICORE has a small stopping area within the spherical sliding surfaces limiting the rotation movement.

The BRYAN prosthesis is clinically used as a compact prosthesis for total replacement of intervertebral discs of the cervical spine. It is attached to the vertebral bodies by convex titanium plates with a porous surface and achieves its biomechanical properties by virtue of a polyurethane nucleus.

The longest experience exists with the CHARITÉ prosthesis, which is the subject matter of the DE 35 29 761 C2 and the U.S. Pat. No. 5,401,269. This prosthesis was developed in 1982 by Dr. Schellnack and Dr. Buttner-Janz at the Charité in Berlin and was later on named SB CHARITÉ prosthesis. In 1984 the first surgery took place. The intervertebral disc prosthesis was further developed and since 1987 the current type of this prosthesis, model III, is being implanted; in the meantime over 10000 times worldwide (DE 35 29 761 C2, U.S. Pat. No. 5,401,269). The prosthesis is functionally three-parted with the sliding partners being metal and polyethylene with two identical spherical sliding surfaces. On the one hand it has a transversally mobile polyethylene core and on the other hand the accordingly adapted concave cups within the two metal endplates. For the adaptation to the intervertebral space, the CHARITÉ prosthesis provides different sizes of the metal plates and different heights of the size adapted sliding cores as well as angled prosthetic endplates, which when implanted vice versa in sagittal direction can also be used as replacement for the vertebral body. The primary fixation of the CHARITÉ prosthesis is achieved by six teeth, which are located in groups of three slightly towards the middle next to the frontal and rear edge of each prosthetic plate.

The other prosthesis have other primary fixations on their surfaces directed towards the intervertebral bodies, e.g. a sagitally running keel, a structured surface, a convex shape with for instance crosswise running grooves and combinations thereof, also with differently located teeth. Furthermore screw fixations can be used, either from ventral or from within the intervertebral space into the intervertebral body.

To assure a long-term fixation of the prosthetic endplates to the intervertebral bodies and to thus generate a firm connection with the bone, a surface was created in analogy to cement-free hip and knee prostheses, which combines chrome-cobalt, titanium and calcium phosphate in such a way that it is possible for bone to grow directly onto the endplates. This direct connection between prosthesis and bone, without the development of connective tissue, makes a long-term fixation of the artificial intervertebral disc possible and reduces the danger of loosening or displacements of the prosthesis and material breakage.

One primary objective of function retaining intervertebral disc replacements is to closely adapt the motions of the prosthesis to the ones of a healthy intervertebral disc. Directly connected to this is the motion and stress for the facet joints, which following inappropriate biomechanical stress have their own potential for disorders. There can be abrasion of the facet joints (arthritis, spondylarthritis), in the full blown picture, with the formation of osteophytes. As result of these osteophytes and also by a pathologic course of motion of the intervertebral disc alone, the irritation of neural structures is possible.

A healthy intervertebral disc is, in its interactions with other elements of the motion segment, composed in such a way that it allows only motions to a certain extent. For example, within the intervertebral disc, motions to the front and back are combined with rotary motions, and side motions are also combined with other motions. The motion amplitudes of a healthy intervertebral disc are very different, with respect to the extension (reclination) and flexion (bending forward) as well as to the lateral bending (right and left) and rotary motion. Although of common basic characteristics, there are differences between the motion amplitudes of the lumbar and cervical spine.

During motion of the intervertebral disc the centre of rotation changes, i.e. the motion of the intervertebral disc does not take place around a fixed center. Due to a simultaneous translation movement of the adjacent vertebrae, the center changes its position constantly (inconstant center of rotation). The prosthesis according to DE 35 29 761 C2 shows a construction which differs in comparison to other available types of prostheses which are build like a ball and socket joint, as a result of which they move around a defined localized centre of rotation. By virtue of the three-part assembly of the prosthesis according to DE 35 29 761 C2, with two metallic endplates and the interpositioned freely mobile polyethylene sliding core, the course of motion of a healthy intervertebral disc of the human spine is mimicked as far as possible, however without the exact motion amplitudes in the specific motion directions.

A further important feature of the healthy lumbar intervertebral disc is its trapezium shape, which is primarily responsible for the lordosis of the lumbar and cervical spine. The vertebral bodies themselves contribute only to a minor extent to the lordosis. During prosthetic replacement of intervertebral discs the lordosis should be maintained or reconstructed. The Charité disc prosthesis provides four differently angled endplates, which moreover can be combined with each other. However during surgery there is more surgical effort and the risk to damage the vertebral endplates with the resulting danger of subsidence of the prosthesis into the vertebral bodies, if the prosthesis has to be removed completely, because a good adjustment of lordosis and an optimal load of the center of the polyethylene core were not achieved.

To avoid sliding or a slip-out of the middle sliding partner from the endplates, the DE 35 29 761 C2 discloses a sliding core with a two-sided partly spherical surface (lenticular), with a plane leading edge and at the exterior with a ring bulge, which will lock between the form-adapted endplates during extreme motion. The DE 102 42 329 A1 discloses a similar intervertebral disc prosthesis which has a groove around the contact surfaces, in which an elastic ring is embedded that is in contact with the opposite contact area for a better course.

The EP 0 560 141 B1 describes a three-part intervertebral disc prosthesis, which also consists of two endplates and an interpositioned prosthetic core. The intervertebral disc prosthesis, described in this document, provides a resistance during rotation of its endplates in opposing directions around a vertical rotary axis without a contact between the prosthetic endplates. This is achieved by a soft limitation of the endplates during rotation onto the prosthesis core caused by the weight, which acts on the plates as a result of the biomechanical load transfer within the spine, because the corresponding radii of curvature differ in a median-sagittal and frontal transection.

The above mentioned models are permanently anchored in the intervertebral spaces as implants. Especially due to a load transfer over too small surface areas, a migration of the endplates into the vertebral bodies and thus a dislocation of the complete implant is possible in middle to long-term, resulting in artificial stress for the vertebral bodies and the adjacent nerves and in the end for the total motion segment, and leading to new complaints of the patients. The long-term stability of the polyethylene and the restricted mobility of the intervertebral disc prosthesis due to an inappropriate load on the polyethylene within the intervertebral space have to be discussed. Insufficiently adapted ranges of motion and adverse biomechanical stress in the motion segment can possibly lead to persistence of the complaints or later on to new complaints of the patients.

The U.S. Pat. No. 6,706,068 B2 on the other hand, describes an intervertebral disc prosthesis comprising an upper and lower part, in which the parts are built correspondently towards each other. No intermediate part as middle sliding partner exists. Different designs are realized for the interdigitating and articulating partners, resulting in a two-part prosthesis. The design is however limited to structures having either edges or corners so that this way both parts of the prosthesis articulate with each other; in this case it is not possible to speak of sliding partners. Furthermore two sliding partners are described having one convex part towards the interior of the prosthesis and the other sliding partner is correspondingly shaped concavely. This kind of prosthesis, however, allows restricted movements of the artificial intervertebral disc only. The concave protuberance corresponds to a part of a ball with the according radius. The U.S. Pat. No. 6,706,068 B2 further shows a two-part disc prosthesis having convex and concave partial areas on each sliding partner corresponding to concave and convex partial areas of the other sliding partner. According to the disclosure of the U.S. Pat. No. 6,706,068 B2 several fixed points of rotation are generated.

The U.S. Pat. No. 5,258,031 discloses a two-part disc prosthesis, in which the two endplates articulate with each other by a ball and socket joint. The joint is located centrally in the frontal section. In a lateral view, the small area of articulation is positioned outside the middle. The articulation areas are spherical in a sagittal view and plane in a frontal view, at the ends small and partly spherical parts are followed by plane skewed ones; these parts have no contact when the other parts of the joint are in contact. Bending to one side with a prosthesis according to the U.S. Pat. No. 5,258,031 is achieved by use of the partly spherical edge of the articulation areas. Whether the lateral inner parts of the endplates come into contact with each other cannot be clearly discerned from the U.S. Pat. No. 5,258,031. At least during one lateral motion, the laterally outwardly opened areas in the bilateral part of the articulation areas do not come into contact. Therefore during lateral bending of the endplates according to the U.S. Pat. No. 5,258,031 the pressure is partly on the spherical edges of the articulation areas only. Because of the pressure distribution only onto points or small areas during side bending, the outer parts of the convex/concave parts are exposed to greater abrasion. The edges of the prosthesis also do not have contact over a large area during the different movements. If the prosthesis according to the U.S. Pat. No. 5,258,031 provides rotation around a vertical axis there is only a bilateral punctiform contact area between the upper and lower endplates.

Thus, there is a need for an intervertebral disc prosthesis for the total replacement of intervertebral discs, with which the extent of the movement can be specifically adapted to the anatomy and biomechanics of the lumbar and cervical spine. This is achieved by the design of the edges of the prosthesis by being such that a physiological motion and at the same time as large as possible a contact region of the sliding partners is provided.

This need is addressed by the present invention. The invention comprises two different types of an intervertebral disc prosthesis, namely a functionally two-part and a functionally three-part prosthesis.

SUMMARY OF THE INVENTION

A functional two-part prosthesis, as per invention, is characterized by
   a) a first sliding partner constructed in such a manner, that the opposite side of the side for the assembly with a vertebral body has a convex curvature (convex articulation area, convexity) and the geometry of this convexity is like a cap of a sphere (spherical convexity), with the convexity being completely surrounded by a edge, and
   b) a second sliding partner with a concave articulation area (concavity) on the side opposite of that assembled to the vertebral body, and the geometry of the concavity being defined by a recess corresponding with the spherical convexity of the first sliding partner, with the recess being completely surrounded by a edge, and
   c) at least one sliding partner having a edge which is suited for the targeted limitation of the maximal possible motion of the sliding partners, which as a result of its varying height surrounds the convexity or concavity in a wavelike manner, and
   d) the other sliding partner having a edge surrounding the corresponding concavity or convexity, which surrounds the corresponding concavity or convexity corresponding with the articulating sliding partner in a wavelike or plane manner,
   e) with the differences of the heights of a wavelike edge changing fluently and/or in one or several steps, and
   f) that during terminal inclination and/or rotation of the sliding partners towards each other a defined limitation of the maximally possible motion arising as a result of a gap-closure of the edges.

The functional three-part prosthesis is characterized by
   a) the middle sliding partner having on the upper and lower side a convex curvature (convexities) and the geometry of these convexities each correlating with the cap of a sphere, and
   b) upper and lower sliding partner constructed with a concave inner articulation area (concavity), and the geometry of these concavities being defined by a corresponding recess to the convexity of the upper and lower side of the middle sliding partner, each being totally surrounded by a edge, and
   c) at least one of the sliding partners having a edge, which is suited for a targeted limitation of the maximally possible motion of the sliding partners, which as a result of its varying heights surrounds the convexity or concavity in a wavelike manner, and
   d) another sliding partner having a edge surrounding the corresponding concavity or convexity, which surrounds the corresponding concavity or convexity corresponding with the articulating sliding partner in a wavelike or plane manner,
   e) with the differences of the heights of a wavelike edge changing fluently and/or in one or several steps, and
   f) that during terminal inclination and/or rotation of the sliding partners towards each other a defined limitation of the maximally possible motion arising as a result of a gap-closure of the edges.

Both prostheses have in common that they comprise of articulation sliding partners of which each upper sliding partner is firmly assembled to an upper vertebral body and each lower sliding partner is firmly assembled to a lower vertebral body and that the sliding partners form interdigitating articulations areas on their toward each other directed inner surfaces. Upper and lower sliding partner of a three-part prosthesis as well as both sliding partners of a two-part prosthesis at the same time act as endplates, having means for assembly to an upper or lower vertebral body.

The two-part prosthesis can be of advantage for the lumbar spine in prosthetic implantations in multiple adjacent intervertebral spaces because of its model-immanent stability. The three-part intervertebral disc prosthesis has the advantage that the transversal sliding of two neighboring vertebrae is minimal, resulting in a particularly advantageous adaptation to the bio-mechanics of the motion segment particularly for the lumbar spine. Furthermore, the three-part prosthesis enables the simulation of an inconstant center of rotation.

With respect to the presented invention the three body axes are described by the following terms: A "sagittal section" or a view in the "sagittal plane" enables a lateral view, because the section plane runs vertically from the front to the back. The term "front" is synonymous with "ventral" and the term "back" with "dorsal", because using these terms, the orientation of the prosthesis within the body is indicated. A "frontal section" or the "frontal plane" is a vertical cross-section from one side to the other. The term "lateral" stands for sidewise. Sagittal and frontal sections are vertical sections as they both run in a vertical plane, but 90 degrees displaced from one another. A view in the "transversal plane" or a "transversal section" shows a top-view onto the prosthesis, as it is a horizontal section.

With respect to the description and depiction of the presented invention an articulation area signifies that region of the sliding partners, which comprises the curved convex and concave parts of the surfaces, which come into contact or articulate with each other. Because of this the articulation area is synonymous with the term sliding area.

The term "corresponding", with respect to the articulating sliding surfaces designates not only congruent convex and concave shaped surfaces articulating with each other. Moreover this term also designates articulating surfaces that are not completely congruent. Such "deviations" or tolerances regarding the sliding surfaces of articulating sliding partners can be caused on the one hand by the chosen materials and shapes. On the other hand it may also be intended that convexity and the concavity articulating with it are not totally congruent, for instance in order to designate the respectively wished for possibilities of motion of the articulating partners directly.

With respect to the presented invention, an edge indicates an area located between outer rim of the particular sliding partner and its convexity(ies) or concavity(ies).

In the case of a two- and three-part intervertebral disc prosthesis, as per invention, the concavities of upper and lower sliding partners are each enclosed by an edge, whereas the convexities of the middle sliding partner of a three part prosthesis span across the complete upper and lower side, i.e. the convexities are without edge or the convexities are each surrounded by an edge. The edges are either in their entire breadth of the same or differing heights or wavelike, with the differences in height of a wavelike edge changing fluently and/or in one or more steps. If in the case of a three-part prosthesis the middle sliding partner has a wavelike edge, the edges of upper and lower sliding partners may be designed without wavelike pattern, because the wavelike shape of the edge of the middle sliding partner is sufficient to define the maximal motion amplitudes of the sliding partners in ventral, dorsal and both lateral directions.

It is important for the design of the surfaces of the edges, that during the terminal inclination of the sliding partners toward each other a maximally possible contact between the edges of the sliding partners is guaranteed. Should the edges not have a plane surface, the have to in any case be designed in such a way that when they close towards each other, a maximally possible contact arises between them. In these cases an edge may have a wavelike shape, which surrounds a convexity or concavity up to the outer rim of the edge. It may also have a wavelike shape, which is rotated by 90 degrees compared to the previous (although this is not exclusive or definite) and moves from inside to outside. The last stated wavelike shape, from inside to outside, is meant to also signify a circular, bow shaped or curved design for the edge, as per invention.

For a two part as well as a three-part intervertebral disc prosthesis, as per invention, aspects of at least one sliding partner arise, as a result of the design of the edge regions of the sliding partners as per invention, in which a wavelike shape of the edge of the edge can be seen because the differently high edge regions transit seamlessly or in one or more steps. As per invention, it is preferred for the two- and three-part prosthesis, that as a result of the wavelike design of at least one edge of a sliding partner, the maximally possible motion of the sliding partners towards each other is always larger in dorsoventral direction than in a laterolateral direction.

An important advantage of certain embodiments of both intervertebral disc prostheses, as per invention, compared to prostheses known from the present state of the art is that during central load transfer over a large surface area as a result of the spherical sliding surface(s), the maximally possible inclination of the sliding partners towards each other in laterolateral and dorsoventral directions can be defined by the design, as per invention, of the differently high edge regions, whose surrounding breadth (of a edge) is equal or different, with the breadths of the edges of the sliding partners are uniform or variable. The differently high edge regions transit seamlessly and/or stepwise and it is solely possible by virtue of the resulting wavelike edge of at least one sliding partner to allow the maximal laterolateral motion-possibility to a lesser degree than the maximally possible inclination of the sliding partners towards each other in a dorsoventral direction. This correlates to the natural situation of an intact motion segment of a healthy lumbar and cervical spine, where the inclination and reclination is always clearly to a larger extent possible than the bending to the sides. Thus by virtue of the prosthesis, as per invention, a situation with respect to the-maximally possible angles of inclination in the different directions is created within the motion segment, which comes very close to the physiological motion possibilities of inclination, reclination and lateral bending.

It is also feasible that as a result of the design of the edge regions of an intervertebral disc prosthesis, as per invention, the angles of inclination may be purposely adapted to the necessities that have to be considered for a patient, who is to have the prosthesis implanted. In such a way, by virtue of the design of the edge region, as per invention, a lateral angle of inclination of 0 degrees could also be set in the extreme case. As the prosthesis, as per invention, is to have as physiological as possible a motion and the resulting impossible bending is not physiological, the 0° motion presents an extreme exception for the design of the edge only.

It is also intended for a three-part prosthesis, as per invention, that the maximally possible angles of inclination of the upper and lower sliding partners are set solely with the wavelike edges of the middle sliding partner. This gives the possibility to only exchange the middle sliding partner with a sliding partner with a different edge design for the adaptation to the spine. The sliding partners assembled to the vertebral bodies do not need to be exchanged, but can remain within the patient, thus foreclosing damage to the vertebral bodies as a result of their removal.

As a result of the respective limitation of the motion possibilities of the edges, as per invention, an advantageous extra protection of the facet joints is achieved because they no longer need to limit the over-proportionate motion within the intervertebral space as is to be found in prostheses with spherical sliding surfaces and always equally high edge of the sliding partners. As a result of this an extreme or wrong stress on the facet joints can be mostly avoided.

With respect to the rotation of the sliding partners towards each other around a fictitious vertical axis, a free rotation of the sliding partners towards each other may theoretically be possible if for instance only one sliding partner has a wavelike edge, depending on the design of the edge region or the shaping of the wavelike regions and the position of the respective maxima of these "waves". If, however, the edge regions of both sliding partners of a sliding area are designed in wavelike manner, it is possible that a specific motion is permitted and then a soft limitation of the rotation takes place, because the raisings and deepenings of the edges are rotated against each other and the prosthesis is "untwisted" against the load bearing down on the sliding partners. This is comparable with the guiding tracks of a screw cap, where the pitches are twisted against each other as well. The limitation of the rotation leads to an improved physiological situation within the motion segment, particularly of the facet joints, because in vivo an axial rotation is only possible to a little extent.

In an intervertebral disc prosthesis, as per invention, the maximally possible angle of inclination (at the same time aperture angle) of the sliding partners toward each other depends on the height of the spherical convexities with respect to their surrounding edges as well as the respective height, inclination and wavelike shaping of the edge surrounding the convexities and concavities.

Regarding the material of the prosthesis, as per invention, it is intended, that the sliding partners are built as a single piece or at least one sliding partner comprises at least two permanent or firmly, but reversibly attached parts, whereas the convexity(ies) and/or the concavity(ies) are the parts being permanent or firmly, but reversibly assembled to the corresponding sliding partner, or the convexity(ies) and/or concavity(ies) have suitable means for a permanent assembly or firm assembly having reversiblity, whereby with each other connected parts comprise the same or different materials or the surfaces of the parts are coated equally or differently. As suitable means for the assembly, adaptations of the shape of the parts to be connected, as per invention, are intended, such as recesses or plane broadenings as part of the edge or being the whole edge. Depending on the chosen design, the respective sliding partner and/or convexity and/or concavity as well as the edge are designated as parts that are to be connected. In addition it is planned for a middle sliding partner that it results from the assembly of the respective parts.

In case that an intervertebral disc prosthesis comprises permanent or firmly, but reversibly attached parts, it is intended that the assembly is achieved by a tongue and groove assembly, a track and corresponding recess, a snap mechanism, by gluing or screwing.

For a three-part intervertebral disc prosthesis, as per invention, it is intended, that upper and lower sliding partner comprise the same material or are equally coated and the middle sliding partner is made of a different material or is differently coated. It is also intended that all three sliding partners comprise the same material or are coated equally.

The sliding partners are manufactured from well established materials in implantation techniques; for instance upper and lower sliding partner are made of rustproof metal and the middle sliding partner of medicinal polyethylene. Other combinations of materials are also possible. The use of other alloplastic materials, which may also be bio-active, is intended too. The sliding partners are high gloss polished at their communicating contact areas to minimize abrasion (low-friction principle). Furthermore a coating of the respective sliding partners with appropriate materials is also planned. Favoured materials are: titanium, titanium alloys, titanium carbide, alloys of cobalt and chrome or other appropriate metals, tantalum or appropriate tantalum alloys, suitable ceramic materials as well as suitable plastics or compound materials.

In a favored design of a three-part prosthesis, as per invention, the spherical-cap shaped convexities on their upper and lower sides of the middle sliding partner have identical or differing radii as well as the corresponding concavities in the upper and lower sliding partners. This increases the possibilities of the adaptation of the motion radii of an intervertebral disc prosthesis, as per invention, to the physiological motion radii.

In the case of identical as well as differing radii of curvature of the upper- and lower side of a middle sliding partner, the maximal height of the convexities on upper and lower side of the middle sliding partner is the same or different. Depending on the design, the height of the edge of a middle sliding partner is reduced by the same amount as the height of the convexity(ies), or the height of the edge remains the same or differs from the change of height of the convexity(ies), and by virtue of this the maximal height of the convexities of the upper and lower side remain the same or are different.

By this measure, as per invention, it is possible to reduce the total height of the whole prosthesis. Such a flatter prosthesis is particularly intended for the implantation in the cervical spine. It is, however, also feasible that such a flat prosthesis be applied for the lumbar region, if the intervertebral spaces are of a low height. On the whole, by this measure, as per invention, the possibility is given to adapt the prosthesis to the height of an intervertebral space by the selection of the respectively high middle sliding partner.

For the intervertebral disc prosthesis, as per invention, a maximal aperture angle of 6°-10° including, for example 6°-7°, 6°-8°, 6°-9°, 7°-8° 7°-9° 7°-10° 8°-9° or 8°-10° during one-sided gap-closure of the sliding partners during extension or flexion, and of 0°-6° including, for example UP to about 5°, up to about 4°, up to about 3°, up to about 2° and up to 1° during one-sided lateral gap-closure is intended, although 0° bending to the side presents more of an extreme and at least 3° bending should be enabled by the prosthesis. The concrete maximal ranges of motion can be constructively adapted for the lumbar and cervical spine, without the need of an "individual prosthesis" for every single intervertebral disc. The aperture angles correspond to the natural segment mobility and are reached by suitable choices of convexities and concavities in connection with the design of the surrounding edges (see above). To compensate for the tolerances within the motion segment an additional 3° will be included for every direction of motion.

For a functional two-part as well as for a functional three-part intervertebral disc prosthesis, as per invention, a limited rotation of the sliding partners towards each other around a fictitious vertical axis of up to 3 degrees including up to about 2 degrees and up to about 1 degree for the lumbar spine and up to 6 degrees including up to about 5 degrees, up to about 4 degrees, up to about 3 degrees, up to about 2 degrees and up to about 1 degree for the cervical spine is intended to each side by virtue of the shaping of the edges, as per invention. To compensate for tolerances within the motion segment an additional 2 degrees to each side will be included.

Furthermore, a shift of up to 4 mm, up to 3 mm, up to 2 mm or up to 1 mm away from a midline sagittal section to dorsal of the convexity(ies) and corresponding concavity(ies) is intended in a two- and three-part intervertebral disc prostheses, as per invention. A dorsally displaced centre of rotation above all corresponds to the physiological situation of the transition between lumbar spine and sacral bone; on the other hand parallel to that, the differences correlating to the physiological situation between the possible angles of inclination during extension and flexion are thus reached.

It is further intended that the edges of the sliding partners outwardly close rectangularly, otherwise inclined, curved, combined straight, curved and/or angled. Particularly in the case of a three-part prosthesis, a design is feasible, in which the upper and lower side of the sliding core simply end perpendicularly or curved towards each other in their periphery and in which the breadth of the edge is not substantially differently designed compared to the upper and lower sliding partner. Thus the middle sliding partner can remain in between the upper and lower sliding partner during terminal inclination too. By virtue of this a compact and economic (w.r.t. space) construction of an intervertebral disc prosthesis, as per invention, is possible.

A slip out of the middle sliding partner out of this "compact" design of a three-part intervertebral disc prosthesis, as per invention, is on one hand prevented by the motion adapted heights of the convexity(ies) and the corresponding concavity (ies) starting with the edge around the articulation areas and on the other hand by the gap-closure between the edges of the sliding partners at terminal inclination. The convexities and the wave form in the edge region are designed in such a way that the convexities interdigitate deeply enough into the articulating concavities, particularly during reclination. A sufficient opening of the whole prosthesis post-operatively, which is a prerequisite for a slip out of the middle sliding partner, is thus not possible.

Furthermore it is intended as per invention, that in the case of a middle sliding partner of a three-part prosthesis, as an additional safeguard, a stop as a part of the outer edge of the middle sliding partner is provided against a slip-out, slip-away or slip-aside (luxation) out of the prosthesis during gap-closure of all three sliding partners. The stop of the middle sliding partner is located next to the periphery of the upper and/or lower sliding partner and it is higher at least on the upper or the lower side than the edge of the middle sliding partner.

This stop, as an additional safeguard against a slip-out, slip-away or slip-aside (luxation) out of the prosthesis can, as per invention also be designed in such a way that it is a part of the edge of the middle sliding partner. It is higher than the edge of the middle sliding partner at the upper or lower side and is lead within a groove in the edge of the upper and/or the lower sliding partner with the necessary liberty for the maximal sliding motion of the sliding partners.

As per invention, a stop is an outwardly directed extension of the edge of a middle sliding partner, which, because of its embodiment, as result of its design, is suited to prevent a slip-out of the middle sliding partner out of the concavities of the upper and lower sliding partner. It is not necessary that a stop encloses the middle sliding partner completely, because this could result in a limitation of the maximal mobility of all sliding partners; where required, it is rather arranged in defined distances or opposite of positions of the edge, which represent possible positions for a slip-out of the middle sliding partner. If the stop is higher on the upper and lower side than the edge of the middle sliding partner, it can for instance be shaped like a drawing-pin, sticking with the tip from outside into the edge, so that the head of the drawing-pin juts out over the upper and lower edge of the middle sliding partner and prevents a slip-out of the middle sliding partner during a terminal inclination in direction of the drawing pin by stopping its movement via contact to the upper and lower sliding partner.

If a stop, as a safeguard to prevent slip-out, is part of the edge of a sliding partner, the height of the convexity depends only—with regard to the anatomy and the material properties—on the required maximal inclination angles, which are also influenced by this (see above).

A stop to secure the middle sliding partner of a three-part prosthesis is advantageously shaped in such a way that it is part of the contact areas during terminal inclination of the edges of the sliding partners. Due to this fact the stop functions not only as a safeguard, but it additionally increases the load bearing area during terminal inclination of the sliding partners; the advantages of this have already been described. The possibility for such a design, however, depends crucially on the external shape of the upper and lower sliding partner and the respective breadth of the edges of the convexity and concavity.

In a further design of a three part intervertebral disc prosthesis it is intended that the height of the middle sliding partner partly or totally continuously increases beginning from the transition area between the convexity and the edge up unto the peripheral edge area. This is intended without the size of the aperture angle changing as a result of an adaptation to the height of the edge of the upper and lower sliding partner. This "dovetail" shape of the edge of the middle sliding partner increases the safeguard against dislocation.

As per invention, a shape for the upper and lower sliding partner is intended for a three-part prosthesis, in which the peripheral edge areas are complete or partly hook-shaped, perpendicular, otherwise angular, curved or a combination thereof in direction of the other peripheral sliding partner. In this design, the edge of the middle sliding partner is narrower there, so that the middle sliding partner is partly or completed covered by the features of one or both outer sliding partners, in order to prevent a slip-out of the middle sliding partner. Advantageously, the edge of the middle sliding partner is adapted in such a way to the shape of the edge of the outer sliding partners, that during terminal gap-closure as high as possible an area of the articulating sliding partners comes into contact.

Further, it is intended for an intervertebral disc prosthesis, as per invention, that the outer circumferences of the upper and lower sliding partner may taper off from dorsal to ventral (lumbar spine) or from ventral to dorsal (cervical spine) in a transversal view. This tapering off of the outer circumferences of the upper and lower sliding partner may laterally be in the form of identical curves and is preferably a segment of a circle. Where necessary, area and shape of the outer circumference of the upper and lower sliding partner can be equal or unequal and thus adapted by this to the size of the respective vertebral body with which they will be assembled.

The tapering off shape of the circumference of the upper and lower sliding partner the prosthetic plates on the whole corresponds to the usable area of a vertebral body in a transversal view and leads in that way to an optimal use of the area at disposal for anchoring of upper and lower sliding partner with the aim of a large area for load transfer.

Adaptations to the sliding partners, as per invention, of the intervertebral disc prosthesis are further intended, in which upper and/or lower sliding partner are built in such a way in a frontal and/or sagittal section, that the out- and inside of the upper and/or lower sliding partner are parallel or unparallel to each other. By this measure an intervertebral disc prosthesis, as per invention, can be adapted to vertebral body endplates, which are not standing parallel in a frontal view or which, in a sagittal view, should form an optimal lordosis and positioning of the sliding areas.

It is further intended, that in a two- and three-part design, as per invention, the convexity (two-part prosthesis) or the middle sliding partner (three-part prosthesis) is parallel or unparallel with respect to a fictitious horizontal. In the case of an unparallel design, the upper- and lower sides stand in an angle with respect to a fictitious horizontal, with the angles being the same above and below or different with a middle sliding partner. The convexity(ies) and corresponding concavity(ies) in the two- and three-part prosthesis are symmetrical or asymmetrical in their surface design. By virtue of the angular convexity or the angular middle sliding partner, adaptations to asymmetries of the intervertebral space, into which the prosthesis will be implanted, are also possible.

For a secure anchorage of the implants within the intervertebral space, an edge and/or plane interdigitation of the exterior sides of the upper and lower sliding partner serves for the connection with an upper and lower vertebral body. The exterior sides themselves are flat or convex in shape and it is possible to coat the interdigitation or the vertebra-directed surfaces with or without interdigitation bio-actively or bluntly. To minimize the risk of a fracture of the vertebral body an anchorage with three ventrally positioned and two dorsally positioned anchoring teeth is preferred. As an alternative laterally continuously arranged rows of teeth are favoured for an improved guidance of the upper and lower sliding partner during implantation between the vertebral bodies, because the forceps of the surgeon can grip in the middle gap between the rows of teeth or into holes of the upper and lower sliding partner at level with the teeth.

To facilitate implantation or explantation of the intervertebral disc prosthesis, the upper and/or lower sliding partner is furbished with a provision for instruments in a further design. These provisions preferably comprise holes or moulds, into which the required instrument of the surgeon can grip so that a secure fixation of the respective sliding partner is possible.

Furthermore as absolute measurements for an intervertebral disc prosthesis, as per invention, a maximal breadth (frontal view) of 14 to 48 mm, including about 16 mm, about 18 mm, about 20 mm, about 22 mm, about 24 mm, about 26 mm, about 28 mm, about 30 mm, about 32 mm, about 34 mm, about 36 mm, about 38 mm, about 40 mm, about 42 mm, about 44 mm or about 46 mm, a maximal depth (sagittal view) of 11 to 35 mm, including about 13, about 15 mm, about 17 mm, about 19 mm, about 21 mm, about 23 mm, about 25 mm, about 27 mm, about 29 mm, about 31 mm, about 33 mm, and a maximal height of 4 to 18 mm, including about 6 mm, about 8 mm, about 10 mm, about 12 mm, about 14 mm or about 16 mm, is intended. These measurements are orientated to the natural conditions of the lumbar and cervical spine and assure that the situation with an intervertebral disc prosthesis, as per invention, comes very close to the in vivo situation.

Further, for an intervertebral disc prosthesis, as per invention, one or more X-ray contrast giving markers are provided, which are located under the surface of each of the non X-ray contrast giving parts of the prosthesis. That way it is possible to exactly control the position of these parts of the intervertebral disc prosthesis after the implantation. Furthermore it is possible to check, if these parts have changed their position or if they are still in the right position in defined timely intervals.

Further useful measures are described in the dependent claims; the invention is described in the following by examples and figures.

DETAILED DESCRIPTION OF VARIOUS AND PREFERRED EMBODIMENTS

Figure 1A:
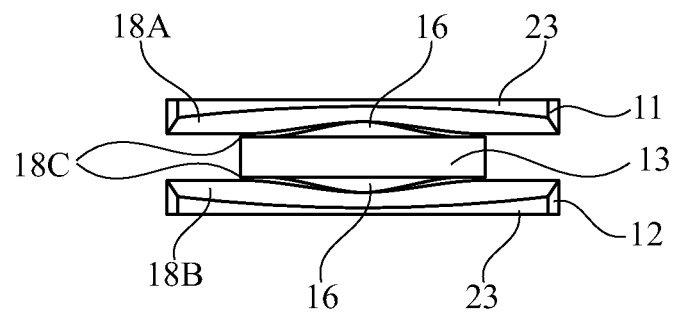
FIG. 1a-c spatial frontal views of a functional three-part prosthesis, as per invention, for the lumbar spine
 a: frontal view from dorsal
 b: frontal view from ventral
 c: median frontal section
FIG. 2a,b spatial sagittal views of a functional three-part intervertebral disc prosthesis, as per invention:
 a: sagittal view
 b: median sagittal section
FIG. 3a,b spatial transversal views:
 a: inner side of upper and lower sliding partner
 b: inner side of upper or lower sliding partner with middle sliding partner on it
FIG. 4a-c transversal view with schematic depiction of different shapes of the upper and lower sliding partner for the lumbar spine
FIG. 5a,b schematic depiction of the arrangement of anchoring teeth on the outside of the upper and lower sliding partners for the lumbar spine
FIG. 6a-e schematic spatial depiction of different waveshaped designs of a middle sliding partner of a three-part intervertebral disc prosthesis, as per invention
FIG. 7a-g schematic spatial depiction of a three-part intervertebral disc prosthesis, as per invention, with stepped design of the edges
FIG. 8 schematic depiction of dorsal or ventral gap-closure in sagittal section indicating the aperture angle α on the ventral or dorsal side
FIG. 9 schematic view of a prosthesis per the invention indicating firm, but reversibly attached parts
FIG. 10 schematic depiction of a middle sliding partner in sagittal view with an edge having a safeguard FIG. 11 transversal view with schematic depiction of an upper or lower sliding partner having dorsally tapering off radii for the cervical spine
FIG. 12 schematic depiction of a middle sliding partner in a middle vertical section having convexities with different heights but same radii on the upper and lower side
FIG. 13 schematic depiction of a prosthesis in a sagittal section with non-parallel inside and outside of the upper and lower sliding partners
FIG. 14 schematic depiction of a middle sliding partner having a wavelike shaped edge with a combination of seamlessly transiting heights of the edge and in several steps
FIG. 15 schematic depiction of a prosthesis in a sagittal section having a middle sliding partner with edge leveling off by the same amount than the edges of upper and lower sliding partners
FIG. 16 schematic depiction of a middle sliding partner in a middle vertical section having convexities with different radii of curvature but same heights on the upper and lower side
FIG. 17 schematic depiction of an additional safeguard for the middle sliding partner which is guided within a groove in an area of the edge of the upper and/or lower sliding partner, wherein a clearance is provided for the maximal sliding motions of the sliding partners.
Figure 1B:
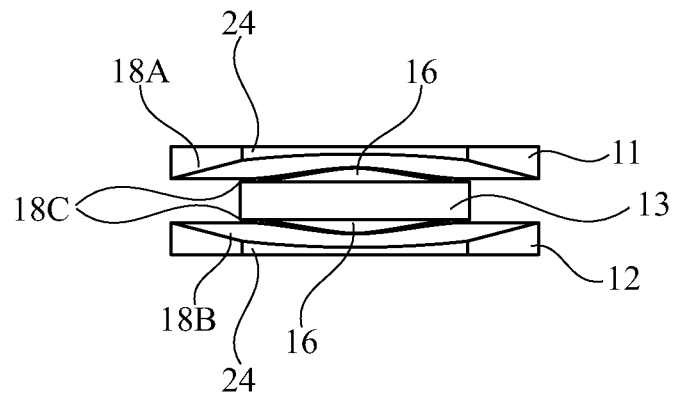
Figure 1C:
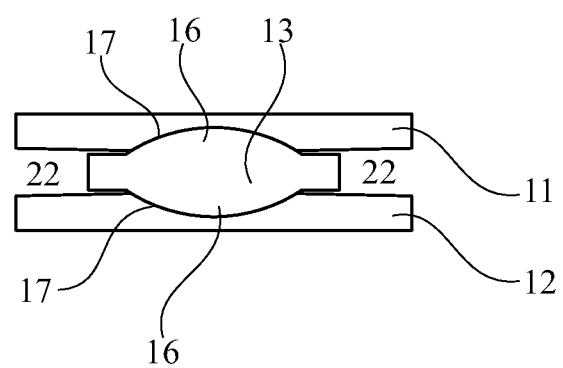
Figure 6A:
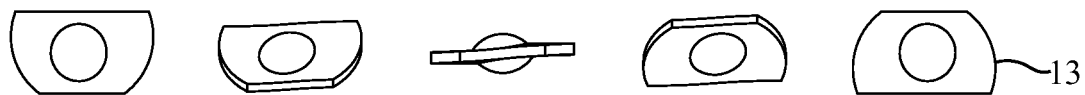
Figure 6B:
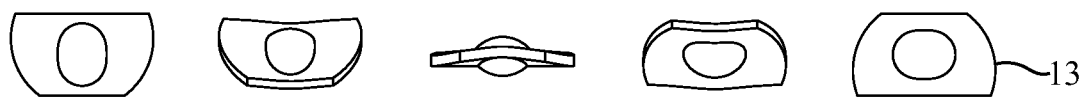
Figure 6C:
Figure 6D:

FIGS. 1a-c show different spatial frontal section views of a model of a functional three-part intervertebral disc prosthesis, as per invention, for the lumbar spine, with the middle sliding partner 13 having an edge 18. As per invention, however, other models of a three-part intervertebral disc prosthesis are also planned, where the middle sliding partner 13 is constructed without an edge 18.

FIG. 1a shows a frontal section view of the dorsal side 23 and FIG. 1 b of the ventral side 24 of an intervertebral disc prosthesis, as per invention. In an intervertebral disc prosthesis, as per invention, intended for the implantation into the lumbar spine, the ventral side 24 (FIG. 1b) is narrower than the dorsal side 23 (FIG. 1a), with the result of the ventrally tapering off shape of the upper and lower sliding partners 11, 12. For an implantation of the intervertebral disc into the cervical spine, the external circumferences of the upper and lower sliding partners 11, 12 tapers off dorsally.

In the models depicted in FIGS. 1a and b the height of the edge 18 of the middle sliding partner 13 is the same around the convexities 16 of the upper and lower side of the middle sliding partner 13. The edges 18A and 18B of the upper and lower sliding partner 11, 12 are constructed laterally higher than dorsally and ventrally. The transitions between the different heights of the edges 18A and 18B are seamlessly, so that a wavelike shape of the edges 18A and 18B arises. This wavelike shape effects the desired laterolateral lesser possible angle of inclination compared to the dorsoventral inclination of the sliding partners 11, 12, 13 towards each other.

FIG. 1c shows a median frontal section of the model depicted in FIGS. 1a and b of an intervertebral disc prosthesis, as per invention. In this section it can be clearly seen that the lateral apertures 22 to both sides of the convexity 16 of the middle sliding partner 13 and concavity 17 of the upper and lower sliding partner 11, 12 are identical.

FIGS. 2a and 2b show a spatial sagittal view (2a) and a median sagittal section (2 b) of a functional three part intervertebral disc prosthesis, as per invention. In both illustrations the upper sliding partner 11, the lower sliding partner 12 as well as the interpositioned sliding partner 13 are depicted. In the depicted model, the middle sliding partner 13 has a edge 18C, which is an optional characteristic.

FIG. 2a shows of the lateral side of the prosthesis. The equally highly shaped edge 18C of the middle sliding partner 13 can be seen as well as each lateral higher edge 18A/B of the upper sliding partner 11 and of the lower sliding partner 12. The transition between the ventral and the dorsal in their heights reduced edges 18A/B of the upper and lower sliding partners, is seamless and bow shaped in this view. Because the edge 18C of the middle sliding partner in the depicted model is of the same height in its complete breadth all around, no wavelike transition of the edges can be seen. If the middle sliding partner 13 moves in dorsal or ventral direction, however, the upper edge 18A and the lower edge 18B form a guide this motion with their wavelike shapes.

FIG. 2b shows a median sagittal section of the intervertebral disc prosthesis, as per invention, depicted in FIG. 2a, with upper and lower sliding partner 11, 12, and an interpositioned middle sliding partner 13. The sliding partners 11, 12, 13 articulate via the convexities 16 and the concavities 17. As the edges of the upper sliding partner 11 and the lower sliding partner 12, as per invention, are dorsally and ventrally not constructed as high as laterally, the seamless transition of the edges 18A/B is depicted.

FIG. 3a shows a transverse section of an upper or lower sliding partner 11, 12 of an three-part intervertebral disc prosthesis, as per invention, or the sliding partner with concavity 17 of a two-part intervertebral disc prosthesis, as per invention. The external shape of the sliding partner 11, 12 tapers off from the dorsal side 23 to the ventral side 24 in the lumbar spine and vice versa in the case of the cervical spine. It can be well seen that the tapering off of the depicted model is in the shape of sections of a circle. The differences in height of the edges 18A/B of a sliding partner 11, 12 are dorsally and ventrally not constructed as highly as laterally.

The concavity 17 is located in the middle, or, alternatively displaced up to 4 mm dorsally (not shown here). This is correspondingly constructed to the convexity 16, which is shaped like the cap of a sphere (FIG. 3b). Because of the differently high edges 18A/B, which completely enclose the concavity 17, the concavity does not appear as a circle, but rather as a dorsally and ventrally flattened round shape.

FIG. 3b shows a transversal section of an upper or lower sliding partner 11, 12, of an intervertebral disc prosthesis, as per invention, in whose concavity a middle sliding partner 13 with an edge 18C is lying. In this aspect too, the tapering off outer shape of the upper and lower sliding partner 11, 12, from the dorsal side 23 and the ventral side 24 (lumbar spine) can be seen. The edges 18A/B have differently high edge regions dorsoventrally and laterally (not shown here). The edge 18C of the middle sliding partner 13 is of equal height around the convexity 16.

The FIGS. 4a-c each schematically show a top view onto alternative designs of the circumference of upper and lower sliding partner 11, 12. The small letters indicate the orientation with respect to the dorsoventral alignment of the plates for the lumbar spine (d=dorsal; v=ventral), which is however reversed for the cervical spine (v=dorsal; d=ventral).

The FIGS. 5a and 5b show alternative arrangements of the anchoring teeth 25 on the outside of the upper and lower sliding partner 11, 12. Again the orientation of the sliding partners with respect to the dorsoventral alignment is indicated by the small letter (d=dorsal; v=ventral). Dorsally, there are no anchoring teeth 25 intended in the middle, because this results on one hand in protecting the vertebral bodies and on the other hand it facilitates the implantation. For the cervical spine the reversed orientation is also without middle dorsal anchoring teeth 25.

FIGS. 6a-d each show a middle sliding partner 13 with a wavelike edge design in different spatial views. The middle sliding partner 13 rotates in this figure from the left to the right, each time around a horizontal axis around 180 degrees. Beginning from FIG. 6a, in which the middle sliding partner has only one wave, the number of waves increases up to FIG. 6d. The transition between the varying heights is seamless.

FIGS. 7a-g each show the same prosthesis with steps of the sliding partners 11, 12, 13, with the height of the edge of the middle sliding partner 13 increasing from the convexity to the outermost part of the edge. By this measure a dislocation of the middle sliding partner 13 from within the prosthesis is to be prevented.

Figure 7A:
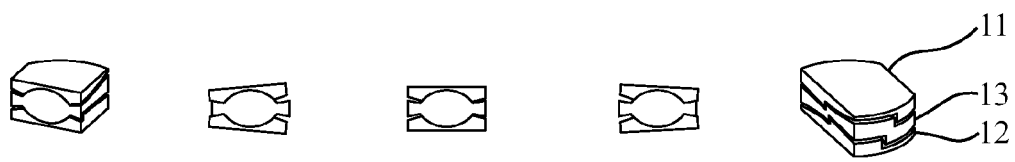

FIG. 7a shows from left to right, the prosthesis in a schematic median sagittal section with motion during inclination to the front and during reclination (outside left: the half prosthesis after a median sagittal section and outside right: the complete prosthesis with an edge of several steps.

Figure 7B:
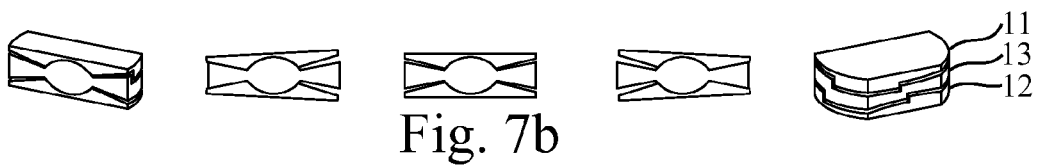

FIG. 7b shows the prosthesis during motion of the sliding partners 11, 12, 13 in a median frontal section. The inclination bending correlates with a right- and left-sided bending.

Figure 7C:
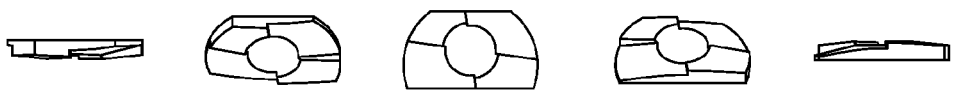

FIG. 7c shows front and back as well as the inside of the upper sliding partner 11 in several views.

Figure 7D:
Figure 7E:
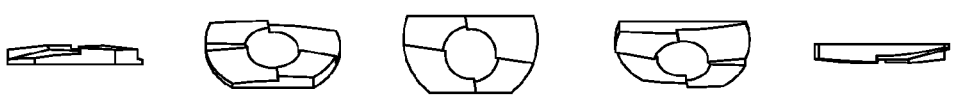

FIG. 7d shows the front and back as well as the articulation areas of the middle sliding partner 13 in different views and FIG. 7e shows the lower sliding partner 12 in a front and back view as well as the inside in several views.

Figure 7F:

FIG. 7f shows the prosthesis from the front, from the side, during bending to the right or left, in reclination and during ventrolateral inclination to the left.

Figure 7G:
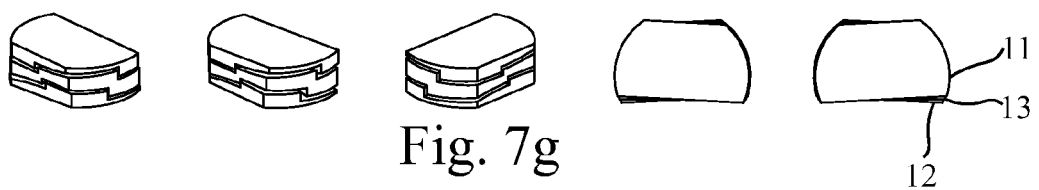
Figure 8:
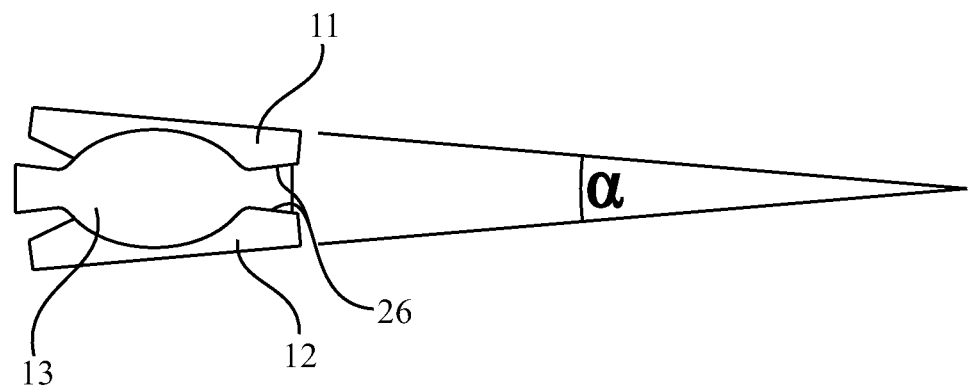
Figure 9:
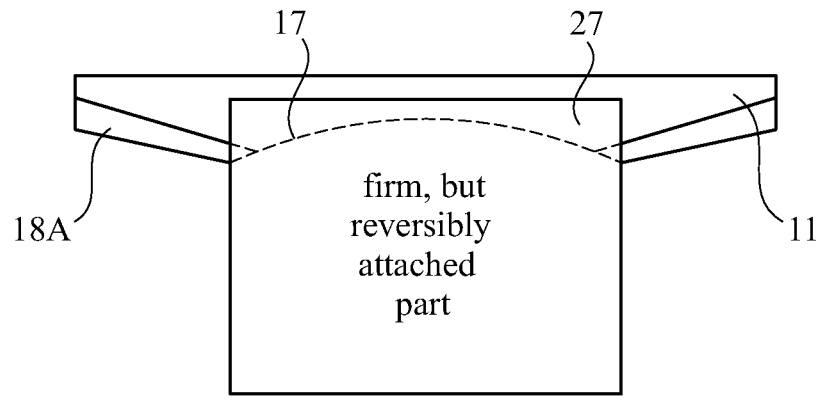
Figure 9:
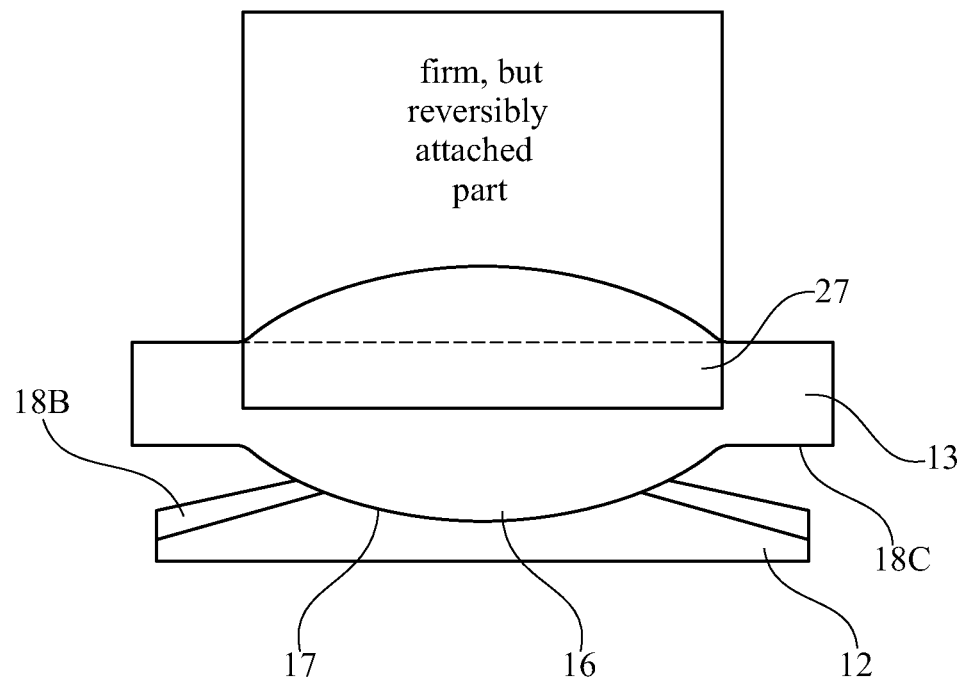
Figure 10:
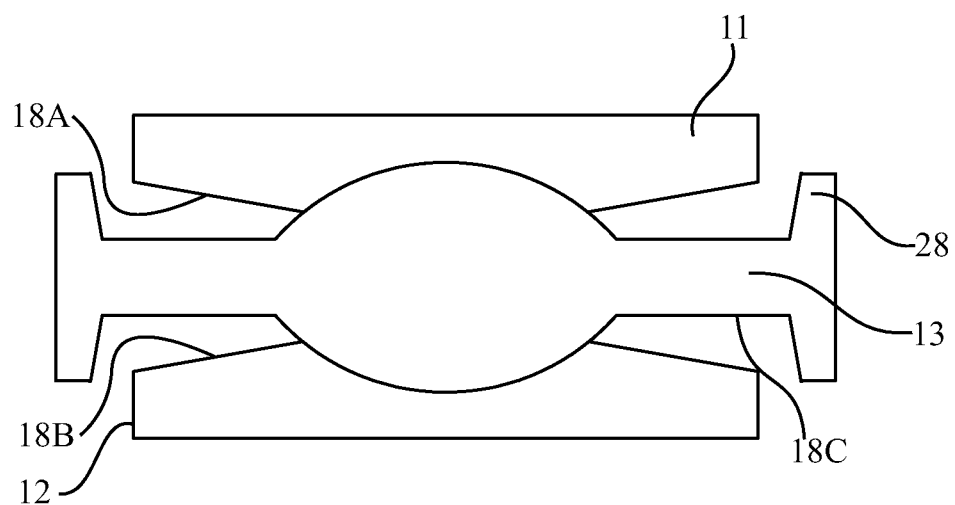
Figure 11:
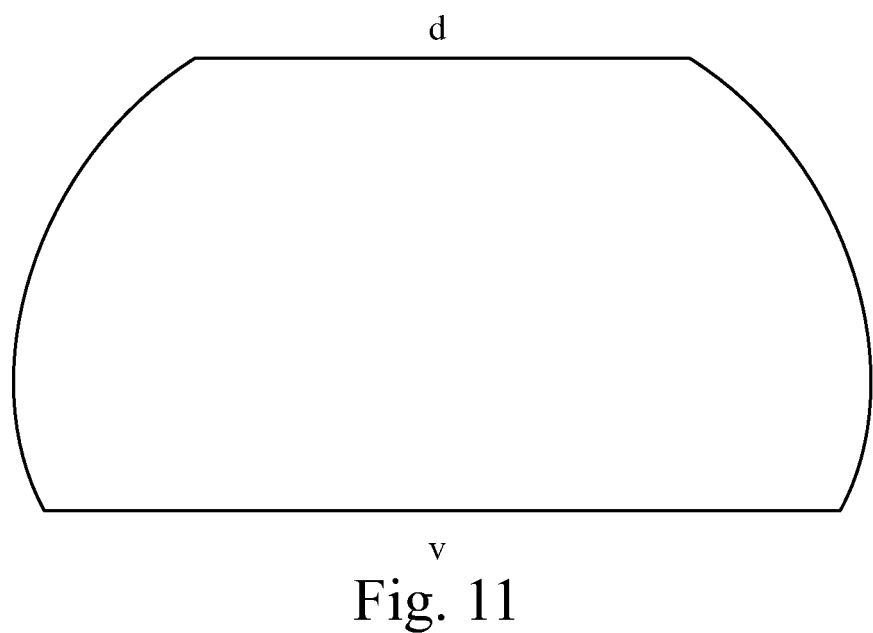
Figure 12:
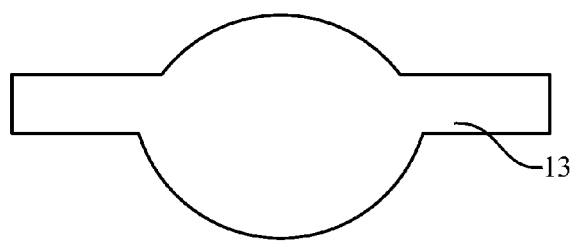
Figure 13:
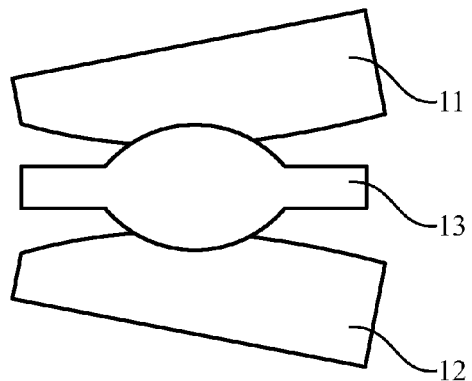
Figure 14:
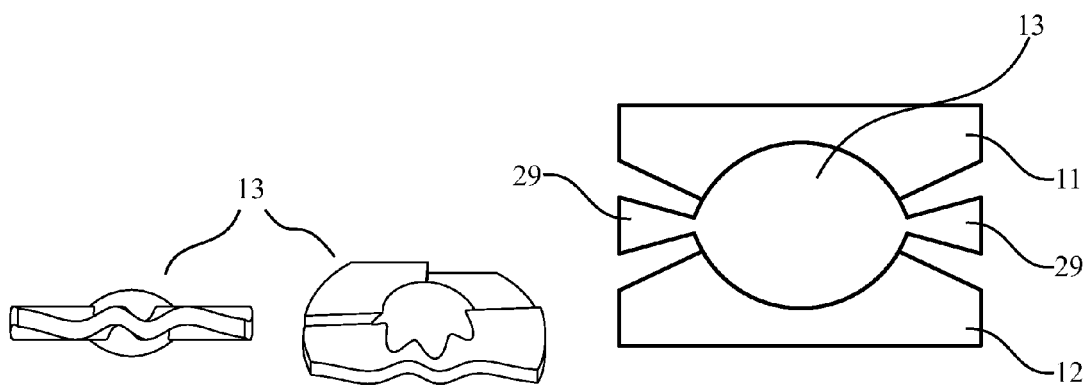
Figure 15:
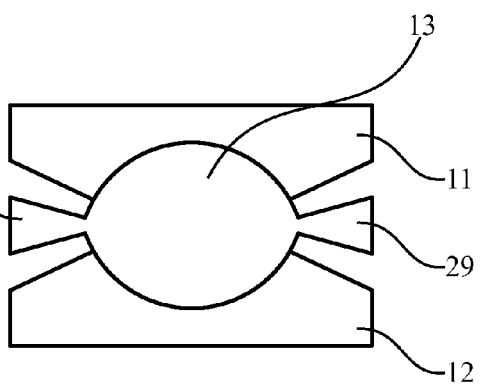
Figure 16:
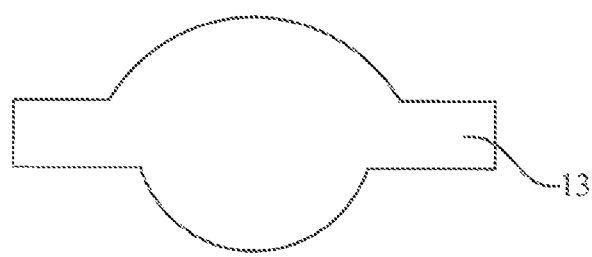
Figure 17:
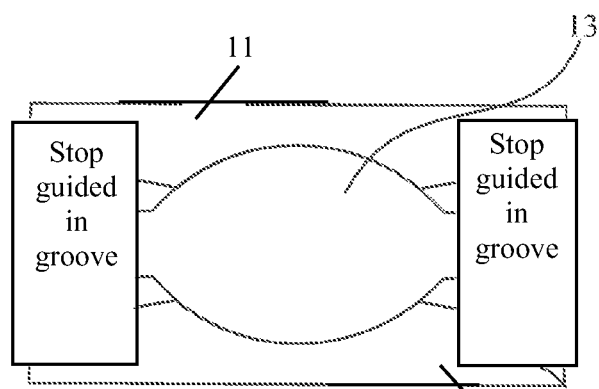
Figure 18:
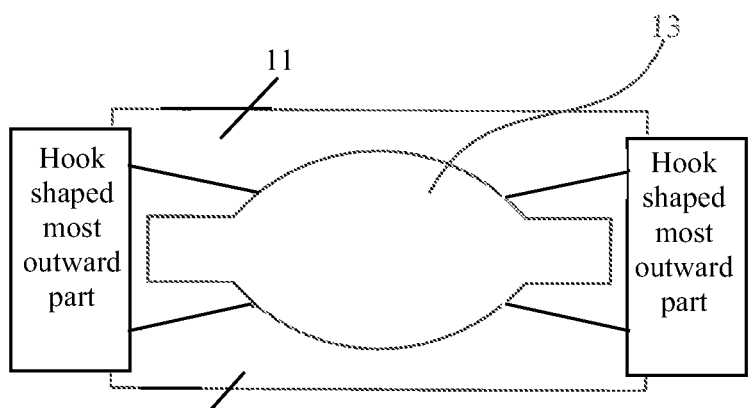
FIG. 18 schematic depiction of an additional safeguard for the middle sliding partner against slip-out of the prosthesis during gap-closure of all three sliding partners, the most outward parts of the middle sliding partner being perpendicular.

In FIG. 7g the prosthesis is depicted during axial rotations. To the far left and to the far right a rotation can be seen, in which the middle sliding partner 13 is in a zero-position and the upper sliding partner 11 is rotating in a clockwise, and the lower sliding partner 12 in an anticlockwise direction. In the second figure from the left the rotation of upper and lower sliding partners 11, 12 is reverse. In the middle the prosthesis can be seen without rotation. The two right parts of the figure each show top views of the axial rotations.

The designs depicted in the illustrations of the intervertebral disc prostheses for a two part as well as for a three part prosthesis above are exemplary only. Once given the above disclosure, many other features, modifications, and improvements will become apparent to the skilled artisan. Such other features, modifications, and improvements are therefore considered to be part of this invention.

REFERENCE NUMBERS 11 upper sliding partner
12 lower sliding partner
13 middle sliding partner
16 convexity
17 concavity
18 edge
22 aperture
23 dorsal side of a sliding partner (lumbar spine)
24 ventral side of a sliding partner (lumbar spine)
25 anchoring teeth 26 gap closure
27 schematic representation of assembly mechanisms
28 stop
29 dovetail

What is claimed is:

1. An intervertebral disc prosthesis for total replacement of the intervertebral disc within the lumbar or cervical spine, comprising an upper sliding partner adapted to firmly assemble to an upper vertebral body, a lower sliding partner adapted to firmly assemble to a lower vertebral body and a middle sliding partner located between the upper and lower sliding partners, wherein said upper, lower and middle sliding partners articulate with respect to each other, and wherein
   a) the middle sliding partner has a spherical convexity on its upper and lower side, each convexity being surrounded by an edge which extends between a spherical transition area of each convexity and an outer rim of the upper and lower sides of the middle sliding partner, wherein at least one of the edges of the upper and lower sides of the middle sliding partner varies circumferentially in height around the respective convexity in a wavelike shape, wherein the height changes (i) seamlessly, (ii) in one or several steps or in a combination of (i) and (ii), and
   b) the upper and lower sliding partners each have a concavity corresponding to the respective convexity of the upper and lower sides of the middle sliding partner, and the concavity of the upper sliding partner and the concavity of the lower sliding partner are each completely surrounded by an edge between a spherical transition area of each concavity and an outer rim of the upper and lower sliding partners, wherein at least one of said edges of the upper and lower sliding partners varies circumferentially in height around the respective concavity in a wavelike shape, wherein the height changes (i) seamlessly, (ii) in one or several steps or in a combination of (i) and (ii), and
   c) said edges of the upper, lower and middle sliding partners together provide a defined maximal possible motion between the upper, lower and middle sliding partners in a ventral, dorsal and lateral direction and a fictitious vertical axis.

2. Intervertebral disc prosthesis according to claim 1, wherein said wavelike shape of the at least one edge of the upper and lower sliding partners engages with said wavelike shape of the at least one edge of the upper and lower sides of the middle sliding partner such that that maximal possible motion between the respective sliding partners towards each other is always larger in a dorsalventral direction than in a laterolateral direction.

3. Intervertebral disc prosthesis according to claim 1, wherein each of the sliding partners is constructed as one piece.

4. Intervertebral disc prosthesis according to claim 1, wherein the convexities and/or the concavities are permanent or removably attached to their respective sliding partners.

5. Intervertebral disc prosthesis according to claim 4, wherein the sliding partners, permanently or removably attached parts or both are made of same materials or are coated equally.

6. Intervertebral disc prosthesis according to claim 3 or 4, wherein the upper, lower and middle sliding partners are made of different materials or are coated differently.

7. Intervertebral disc prosthesis according to claim 4, wherein a tongue and groove assembly, a track and corresponding recess, a snap mechanism, gluing or screwing provides for a permanent or removable attachment of the convexities and/or concavities to the respective sliding partners.

8. Intervertebral disc prosthesis according to claim 1, wherein the spherical convexities on the upper and lower sides of the middle sliding partner as well as the corresponding concavities of the upper and lower sliding partners have different radii.

9. Intervertebral disc prosthesis according to claim 1, wherein the maximal height of the convexities of the middle sliding partner is different on the upper and lower sides.

10. Intervertebral disc prosthesis according to claim 1, wherein, upon gap-closure of the sliding partners, a maximal aperture angle on one side is: (1) during extension or flexion, between 6 and 10 degrees and (2) during lateral gap-closure, between 0 and 6 degrees, with a tolerance of additional 3 degrees in dorsal, ventral and each lateral direction.

11. Intervertebral disc prosthesis according to claim 1, wherein said wavelike shape of the at least one edge of the upper and lower sliding partners engages with said wavelike shape of the at least one edge of the upper and lower sides of the middle sliding partner to allow for a limited rotational motion of the sliding partners around a fictitious vertical axis of up to 3° for the lumbar spine and of up to 6° for the cervical spine to every side, with a tolerance of additional 2 degrees clock and counter clockwise.

12. Intervertebral disc prosthesis according to claim 1, wherein the convexities and the respective corresponding concavities are dorsally displaced up to 4 mm away from an intervertebral disc center of a mediosagittal section.

13. Intervertebral disc prosthesis according to claim 1, wherein as an additional safeguard for the middle sliding partner against slip-out of the prosthesis during gap-closure of all three sliding partners, a stop is part of the edge of the middle sliding partner, that is located outside the upper and/or lower sliding partner.

14. Intervertebral disc prosthesis according to claim 1, wherein as an additional safeguard for the middle sliding partner against a slip-out of the prosthesis during a gap-closure of all three sliding partners the edges on the upper and/or lower side of the middle sliding partner partly or totally increases in height from a transition area of the convexity to the periphery of the edges, with the edges of the upper and/or lower sliding partner levelling off by the same amount as the edge of the middle sliding partner.

15. Intervertebral disc prosthesis according to claim 1, wherein as an additional safeguard for the middle sliding partner against a slip-out out of the prosthesis during a gap-closure of all three sliding partners, the most outward portion of the edges of the upper and/or lower sliding partner are completely or partly hook-shaped, perpendicular, otherwise angular, curved or a combination thereof in a direction of the upper and/or lower sliding partner.

16. Intervertebral disc prosthesis according to claim 1, wherein upper and/or lower sliding partners are constructed in such a way that in frontal and/or sagittal view an outside and inside of the upper and/or lower sliding partner run non parallel.

17. Intervertebral disc prosthesis according to claim 1, wherein the outer surface of the upper and lower sliding partners are plane or convex and coated bio-actively.

18. Intervertebral disc prosthesis according to claim 1, wherein, upon assembly of the intervertebral disc, the intervertebral disc has a maximal breadth of 14 to 48 mm, a maximal depth of 11 to 35 mm and a maximal height of 4 to 18 mm.

19. Intervertebral disc prosthesis according to claim 1, wherein the intervertebral disc prosthesis is suitable for the implantation into the lumbar spine, with an outer circumference of the upper and lower sliding partners tapering off ventrally in the transversal view.

20. Intervertebral disc prosthesis according to claim 1, wherein the intervertebral disc prosthesis is suitable for the implantation into the cervical spine, with an outer circumference of the upper and lower sliding partners tapering off dorsally in the transversal view.

21. Intervertebral disc prosthesis according to claim 1, wherein the prosthesis is marked under a surface of at least one of the sliding partners with one or more radiolucent tags.

22. Intervertebral disc prosthesis according to claim 1, wherein an outer surface of the upper and lower sliding partners is blunt and the upper and lower sliding partners have, for their primary anchorage with vertebral bodies, rows of anchoring teeth that are either arranged from dorsal to ventral laterally straight or at an incline or ventral and dorsal in lateral alignment, and wherein the respective dorsal row has only laterally arranged anchoring teeth.

23. Intervertebral disc prosthesis according to claim 1, wherein during axial rotation of the upper, lower and middle sliding partners towards each other, a defined limitation of the maximal possible motion arises as a result of a gap-closure of the edges.

24. Intervertebral disc prosthesis according to claim 1, wherein the spherical convexities on the upper and lower sides of the middle sliding partner as well as the corresponding concavities of the upper and lower sliding partners have identical radii.

25. Intervertebral disc prosthesis according to claim 1, wherein the maximal height of the convexities on the upper and lower sides of the middle sliding partner is equal.

26. Intervertebral disc prosthesis according to claim 1, wherein upper and/or lower sliding partners are constructed in such a way that in frontal and/or sagittal view an outside and inside of the upper and/or lower sliding partners run parallel.

27. Intervertebral disc prosthesis according to claim 1, wherein a maximal possible aperture angle of the upper, lower and middle sliding partners depends on
a) a height of the spherical convexities with respect to the surrounding edges, as well as
b) a height of said wavelike shape of the at least one edge of the upper and lower sliding partners, a height of said wavelike shape of the at least one edge of the upper and lower sides of the middle sliding partner, and an inclination of the edges of the upper, lower and middle sliding partners towards each other.

28. Intervertebral disc prosthesis according to claim 4, wherein the permanent or removably attached parts are made of different materials or are coated differently.

29. Intervertebral disc prosthesis according to claim 3, wherein the sliding partners are made of the same material or are coated equally.

30. Intervertebral disc prosthesis according to claim 1, wherein the edges of the upper and lower side of the middle sliding partner, the edge of the upper sliding partner and the edge of the lower sliding partner vary circumferentially in height in said wavelike shape, wherein the height changes (i) seamlessly, (ii) in one or several steps or in a combination of (i) and (ii).

* * * * *